United States Patent [19]
Sites et al.

[11] Patent Number: 6,011,620
[45] Date of Patent: Jan. 4, 2000

[54] METHOD AND APPARATUS FOR THE AUTOMATIC INSPECTION OF OPTICALLY TRANSMISSIVE PLANAR OBJECTS

[75] Inventors: Peter Winston Sites, Knoxville; Anthony Scott Nelms, Maryville, both of Tenn.

[73] Assignee: Northrop Grumman Corporation, Los Angeles, Calif.

[21] Appl. No.: 09/055,536

[22] Filed: Apr. 6, 1998

[51] Int. Cl.[7] .................................................. G01N 21/00
[52] U.S. Cl. ........................................ 356/239.1; 356/430
[58] Field of Search .................................... 356/237, 239, 356/240, 429–431; 250/223 B, 559.42

[56] References Cited

U.S. PATENT DOCUMENTS

| | | |
|---|---|---|
| 3,492,490 | 1/1970 | Bayha et al. . |
| 4,492,477 | 1/1985 | Leser ........................................ 356/430 |
| 4,549,206 | 10/1985 | Suzuki et al. ........................... 356/239 |
| 4,902,137 | 2/1990 | Krieg et al. .............................. 356/427 |
| 4,924,083 | 5/1990 | Ishikawa et al. ........................ 356/240 |
| 5,004,909 | 4/1991 | Fukuchi ............................... 250/223 B |
| 5,243,400 | 9/1993 | Ringllien ................................. 356/428 |
| 5,452,079 | 9/1995 | Okugawa ................................. 356/430 |
| 5,691,811 | 11/1997 | Kihira .................................. 356/239.1 |
| 5,715,051 | 2/1998 | Luster .................................... 356/239 |
| 5,767,961 | 6/1998 | Nishikawa et al. ...................... 356/430 |

*Primary Examiner*—Hoa Q. Pham
*Attorney, Agent, or Firm*—Walter G. Sutcliff

[57] ABSTRACT

Inspection apparatus for determining defects in a planar light transmissive object. A diffuse light is projected through a mask toward an object under test at an inspection location. A digital video camera observes the inspection location and obtains images of the object. These images are examined and processed by a signal processor to obtain indications of various defects. The mask utilized is of a selected design having either multiple alternating narrow clear and opaque stripes, or a single narrow clear stripe straddled by opaque regions or a single narrow opaque stripe straddled by clear regions.

9 Claims, 15 Drawing Sheets

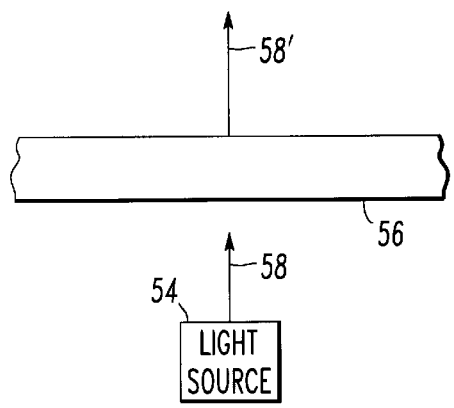
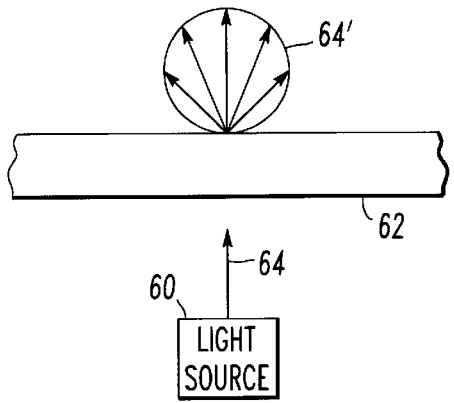
FIG.6A          FIG.6B
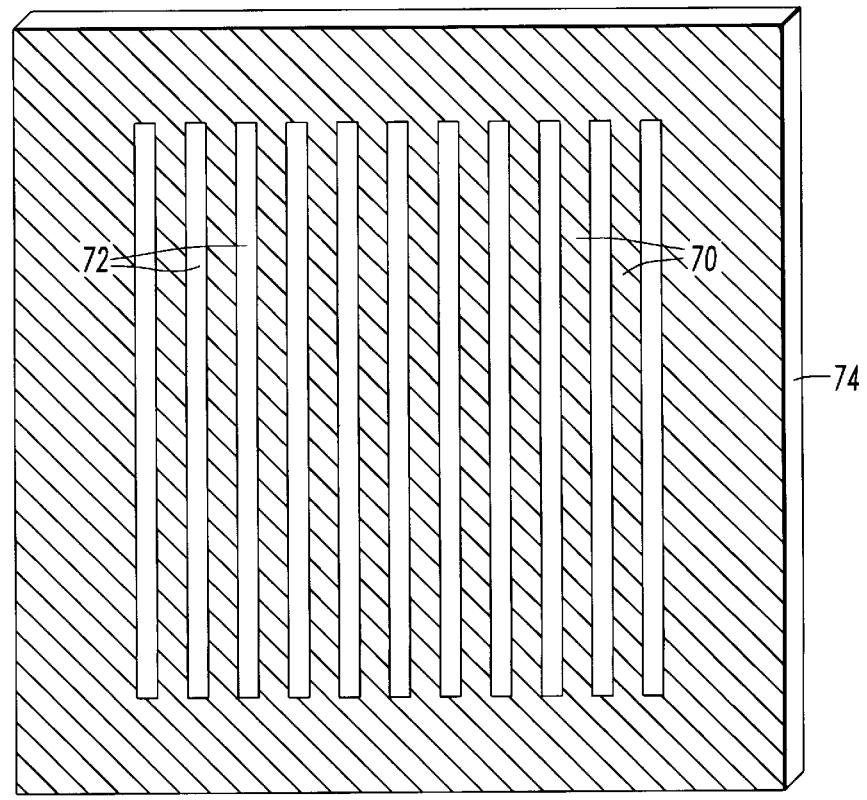
FIG.7

METHOD AND APPARATUS FOR THE AUTOMATIC INSPECTION OF OPTICALLY TRANSMISSIVE PLANAR OBJECTS

BACKGROUND OF THE INVENTION

1. Field of the Invention

The invention in general relates to inspection systems and more particularly to a system which automatically inspects planar objects to determine various defects.

2. Description of Related Art

In the field of sheet glass or plastic manufacture, as well as components made therefrom, a need exists for determining the presence, as well as severity, of defects to obtain an indication of overall quality.

Current methodologies typically involve the use of human inspectors to identify and cull out inferior products. These methods are prone to the inconsistencies and subjectivity inherent in human inspection. Furthermore, certain types of defects may not even be discernible to the human eye.

To improve the quality assessment process, some manufactures utilize machine vision technology whereby the assessment is done automatically using digital video cameras for image capture and image processing for defect determination. This process is a significant improvement over the human operator method, but is still not capable of properly or sufficiently enhancing the entire range of defect types.

The present invention provides greater sensitivity to defect detection and is capable of detecting a greater range of defect types.

SUMMARY OF THE INVENTION

Apparatus for detecting defects in optically transmissive planar objects is provided and includes a camera for obtaining images of the object and a light source positioned to direct its light toward the camera. An object inspection location is disposed between the light source and camera for receiving the object, or a portion thereof, to be inspected. A mask is positioned between the light source and inspection location, with the mask having either a) a narrow clear stripe, for allowing transmission of the light, and straddled by opaque regions which block transmission of the light, b) a narrow opaque stripe straddled by clear regions, or c) a series of alternating narrow clear and opaque stripes. For this latter mask, the light source provides a monochromatic light. Means are provided for relatively moving the object through the inspection location during which time the camera is operable to obtain an image of the object. A processing arrangement is provided for processing the obtained images for providing indications of predetermined defects in the objects.

BRIEF DESCRIPTION OF THE DRAWINGS

FIGS. 6A and 6B serve to illustrate the production of diffused light.

FIG. 7 illustrates one type of mask, a transition mask, which may be utilized herein.

DESCRIPTION OF THE PREFERRED EMBODIMENT

Figure 1:
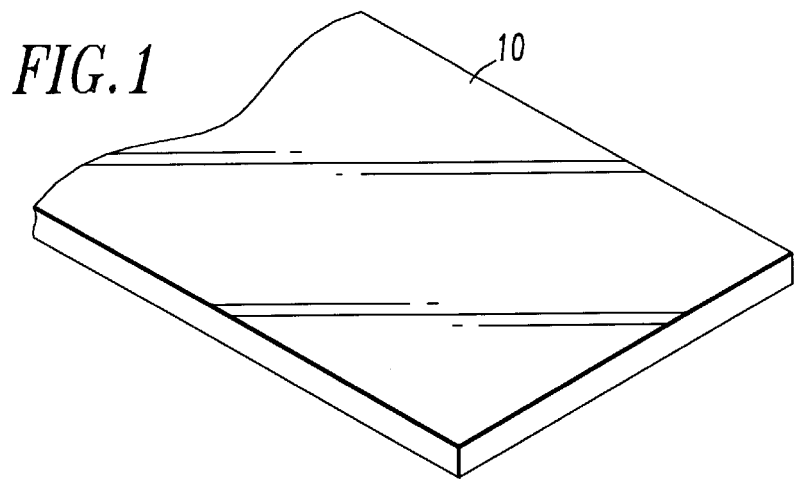
FIGS. 1, 2 and 3 illustrate various objects which may be examined for defects by the present apparatus.

In the drawings, which are not to scale, like or corresponding parts are denoted by like or corresponding reference numerals.

The present apparatus utilizes machine vision technology to automate the inspection process of various transparent planar objects. By way of example, FIG. 1 illustrates a transparent sheet 10 representative of rigid sheet glass or plastic, as well as relatively thin plastic wrap.

Figure 2:
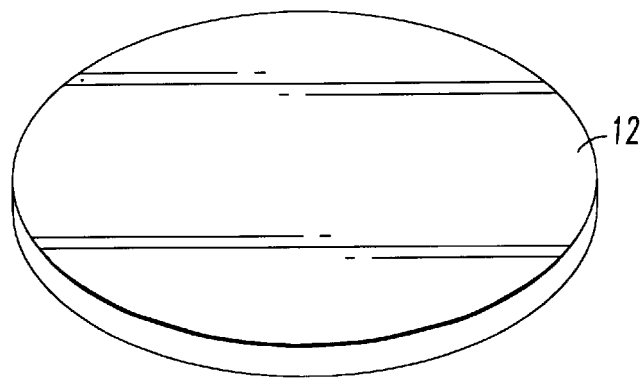
Figure 3:
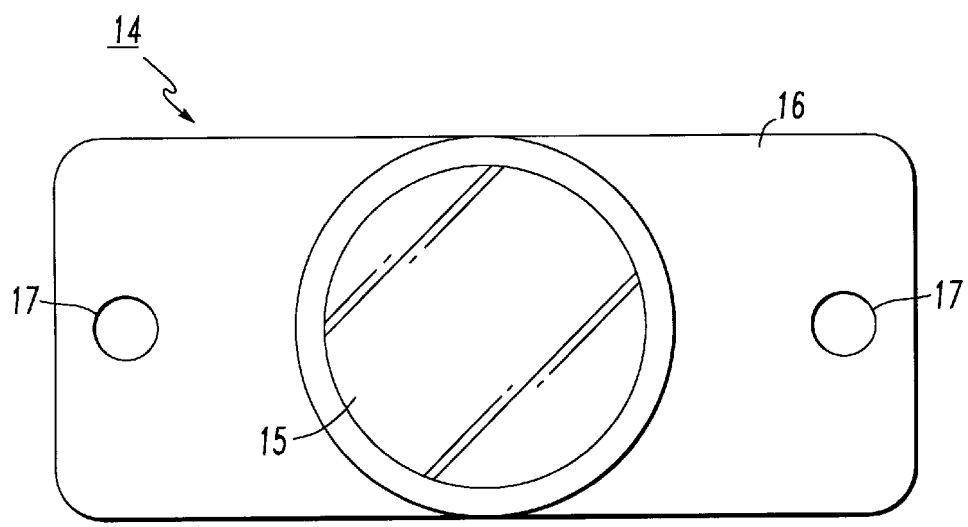

FIG. 2 is representative of an optical flat 12 which may be used in the fabrication of eyeware, filters, or optical instruments such as telescopes, etc., and FIG. 3 is representative of an intraocular lens (IOL) 14. In addition to a lens portion which is the optic zone 15, the IOL 14 includes a non-optic portion in the form of a planar flange constituting what is known as a haptic zone 16. Anchor holes 17 secure the IOL to the interior of the eye. The inspection of the lens portion of objects such as the IOL is more fully described and claimed in commonly assigned copending application Ser. No. 08/995,081 filed Dec. 19, 1997. The present invention is applicable for the inspection of the haptic zone of such IOLs.

Figure 4:
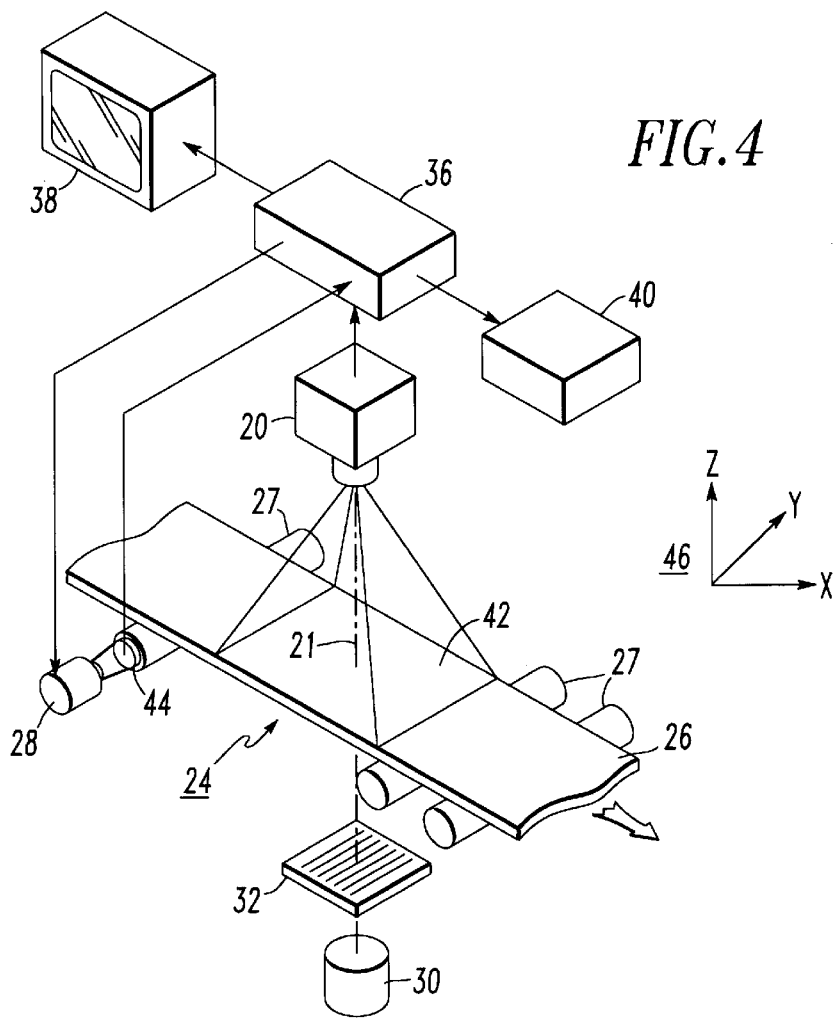
FIG. 4 illustrates one embodiment of the present invention.

One embodiment of the present invention is illustrated in FIG. 4. The apparatus includes a digital video camera 20 having an optical axis 21. The camera 20 views an inspection location 24 through which passes an object to be examined for defects. In FIG. 4 the object is, by way of example, a glass or plastic sheet 26 which is moved on rollers 27 by a drive mechanism 28.

Positioned on the other side of the inspection location 24, and along the optical axis 21 of the camera 20, is a light source 30 which in the preferred embodiment, provides a diffuse light. Light from this source 30 passes through a mask 32, having a particular design, as will be described, such that an image is captured by the camera 20.

A signal processor 36 is operable to take a captured image and perform various diagnostic routines well known to those skilled in the art, to determine the presence of a multitude of possible defects using images obtained with the mask 32 in position. These images may, if desired, be displayed on a high resolution display 38. A personal computer 40 may be included and allows for operator interaction with the signal processor 36 to enter data such as object lot number, camera settings, and to obtain information on defects, product runs, and summaries, by way of example.

The optics and settings of the camera 20 are such that it examines a viewing area 42 on the object 26. After an image of this area is captured, the object may be indexed by the drive mechanism 28, under control of processor 36, such that a new area of the object is brought to the inspection location 24. If desired, a shaft encoder 44 may be included for providing positional information to the signal processor 36. Other drive means for bringing an object, or a pallet carrying the object, to an inspection station may be utilized. One such arrangement, for examining IOLs, is illustrated in the aforementioned application.

For the orientation illustrated, and with reference to the XYZ coordinate system 46, the optical axis 21 of the camera 20 lies along the Z axis, the object is moved along the X axis and viewing area 42 lies in an XY plane. For objects wider than the viewing area, multiple cameras with light sources and masks may be provided for the entire width of the object, in the direction of the Y axis.

Figure 5:
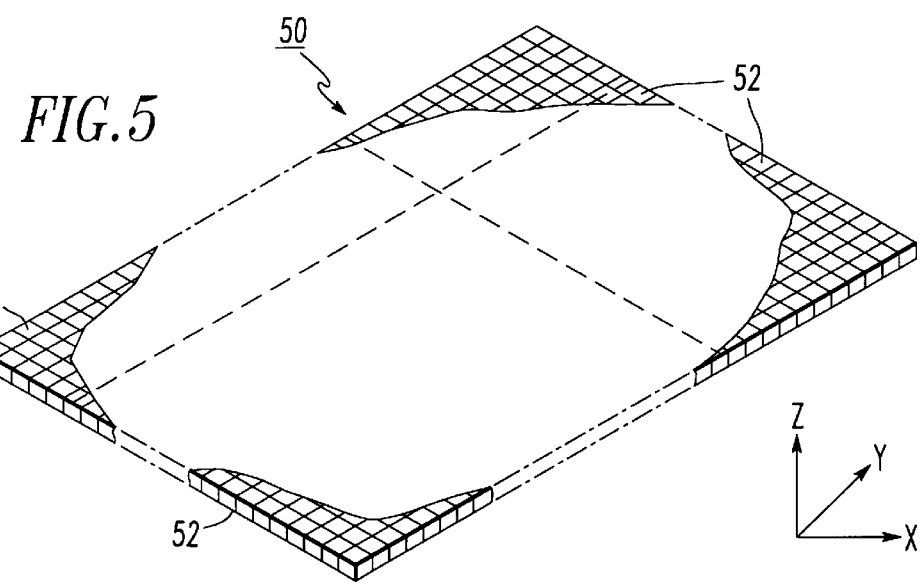
FIG. 5 illustrates a sensor array which is incorporated in the camera shown in FIG. 4.

An entire image of the viewing area 42 is obtained at one time and thereafter processed. This capture is performed by a sensor array as illustrated in FIG. 5. That is, the sensor array 50, located in the camera 20 is constituted by an XY array of individual identical sensor elements 52, such as CCDs. Commercially available digital video cameras have sensor arrays which typically range from 1024×1024 elements to 4096×4096 elements, depending upon the resolution desired.

As previously stated, light is projected through the objects under test. In the preferred embodiment of the invention a light source arrangement is incorporated which provides diffused light for the object examination. FIGS. 6A and 6B serve to illustrate this concept. In FIG. 6A a light source 54 projects light through a clear plate 56. A single ray of light, as represented by arrow 58 passes through the clear plate 56 and emerges as a single ray 58'.

In FIG. 6B however, a similar light source 60 projects light through a diffuser plate 62 and a single ray of light, as represented by arrow 64 emerges from the diffuser plate 62 as a plurality of rays 64' emerging in different directions and with different intensities, depending upon the type of diffuser plate utilized. The diffuser plate may be placed over the light source, or, as utilized herein, may be integral with the masks that are used.

One type of mask which is utilized in the present invention for the embodiment of FIG. 4 is a transition mask 32. A transition mask as used herein is composed of alternate bands of clear (light transmitting) and opaque (light blocking) portions. In one embodiment these alternating bands take the form of parallel stripes as illustrated by transition mask 32 in FIG. 7, with opaque stripe portions 70 and clear stripe portions 72 being positioned upon a diffuser plate 74.

Figure 8:
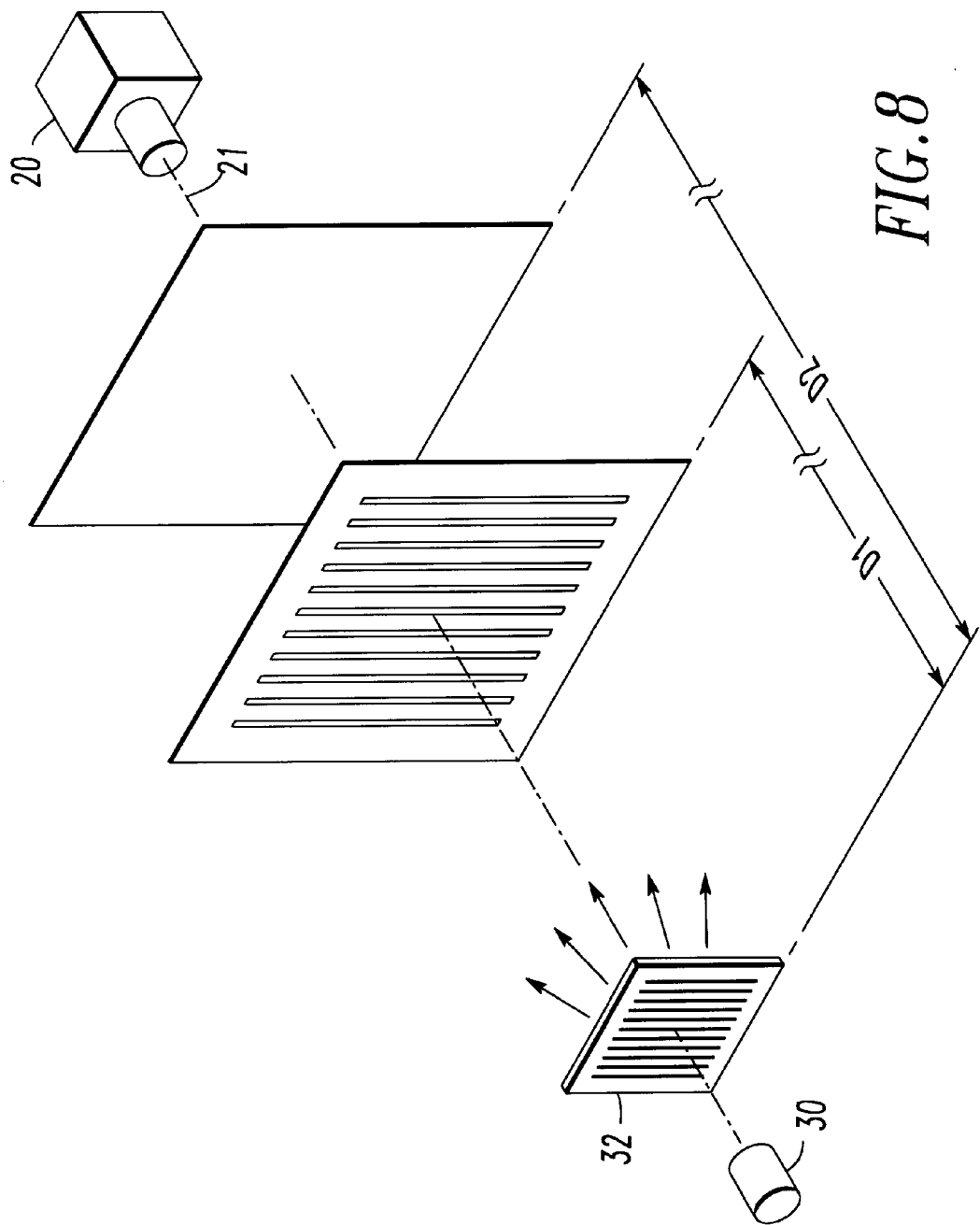
FIG. 8 serves to illustrate the patterns obtained using the transition mask of FIG. 7.

When using this transition mask, the light source 30 will be of the type which provides a monochromatic light. The nature of the transition mask is such that the diffused monochromatic light from the clear stripes 72 between the opaque stripes 70 interact in a constructive and destructive manner at different distances from the mask. With reference to FIG. 8, the combination of light source 30 and transition mask 32 will produce a cyclical pattern going from stripes to a uniform pattern, as a function of distance. This is shown for two different distances D1 and D2. At D1 the pattern is comprised of distinct stripes, while at distance D2 the pattern is essentially uniform. The camera 20 positioned along the optical axis 21 can be focused to an object plane where the pattern of constructive and destructive light rays will show up, at the camera image plane (where the CCD array 50 is located) as a striped pattern, as an essentially uniform pattern or somewhere in-between, depending on the position of the camera along the optical axis. For this to occur the light striking the CCD array of the camera 20 must be monochromatic light such as may be provided by a monochromatic light source or by an appropriate filter positioned on the optical axis.

Figure 9:
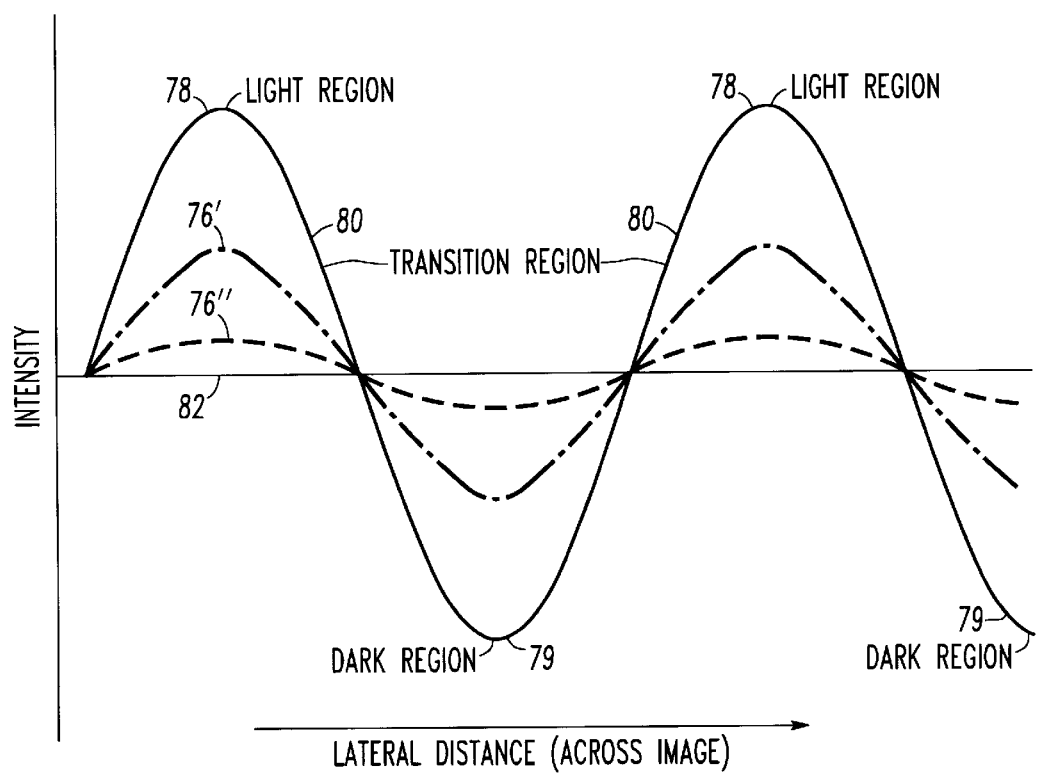
FIG. 9 shows the variation in amplitude as a function of distance for the arrangement of FIG. 8.

The cyclical nature of the pattern caused by the transition mask 32 may be demonstrated with reference to FIG. 9 wherein curve 76 represents the intensity of light with respect to lateral distance, at one point along the optical axis. The positive peaks 78 of curve 76 represent maximum intensity and are indicative of clear stripes, whereas the negative peaks 79 represent minimum intensity and are indicative of dark stripes. The transition from clear to opaque stripes is represented by the sloping portions 80 of the curve and it is in this region that defects are most pronounced.

At a different position along the optical axis, the intensity of the clear and opaque stripes is diminished, as represented by curve 76'. Curve 76" shows the intensity at still another location, whereas the horizontal line 82 represents an essentially uniform pattern at some other position.

The transition mask is especially well adapted to detect various subtle defect types such as flow marks, warpage, scratches, embedded inclusions and small surface voids which are not detectable by other inspection techniques. When using the transition mask, and as illustrated in FIG. 10A, the apparatus takes advantage of the constructive/destructive interference effect as described in FIG. 8.

Figure 10A:
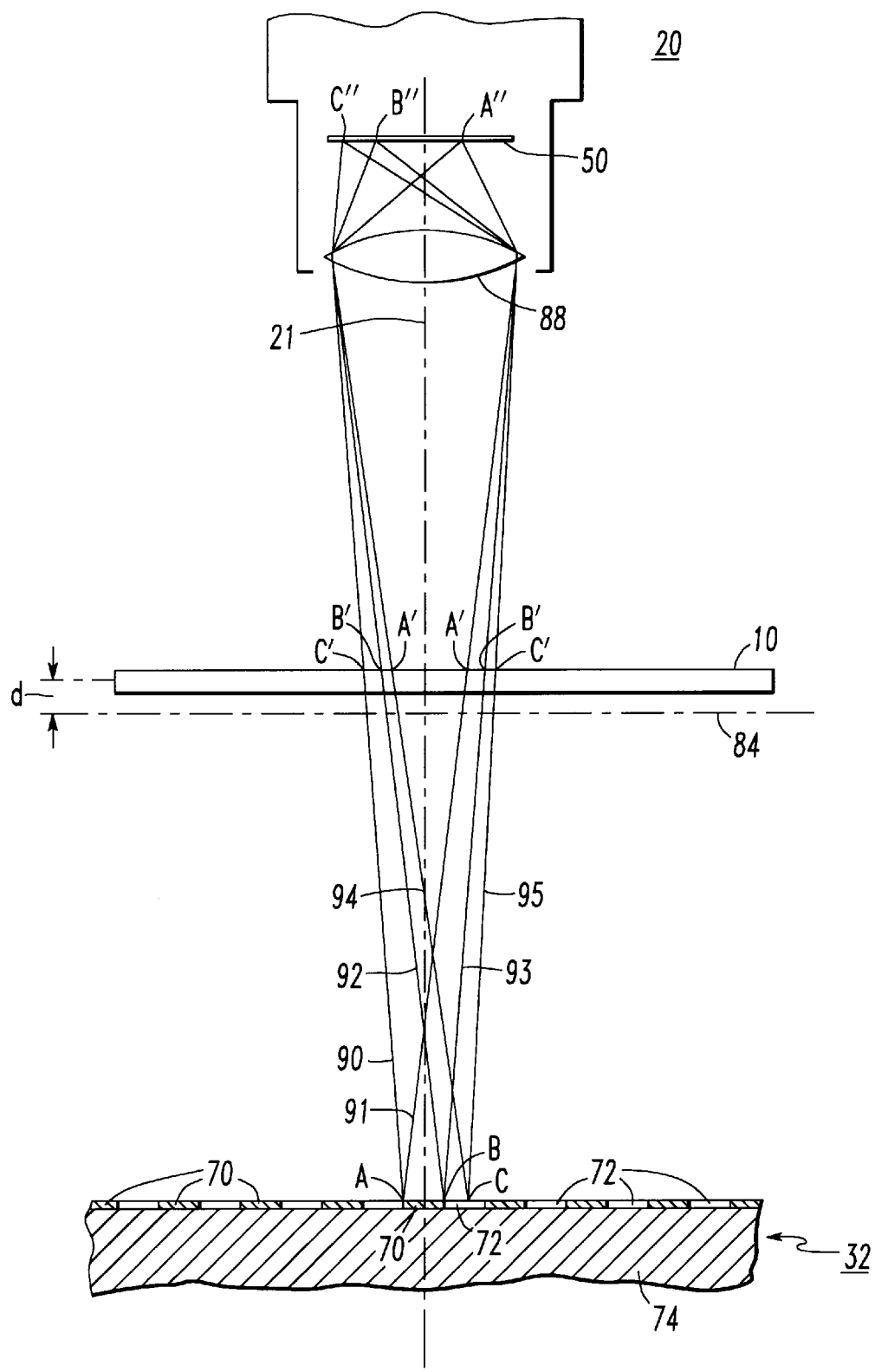
FIGS. 10A, 10B and 10C are ray diagrams illustrating the operation of the apparatus with the transition mask.

In FIG. 10A, the camera 20 is focused on an object plane 84 at which an essentially uniform image of the striped pattern exists (one uniform image being illustrated at a distance D2 from the light source in FIG. 8). The object 10 can now be inspected against a uniform background while still maintaining sensitivity to subtle defects. For the inspection process the object is displaced above the object plane 84 by a small distance d (or a small distance below the object plane).

Surface contour changes or embedded inclusions cause light passing through the transition mask 32 to be redirected from its existing path and in turn disturb the interference phenomena that occurs at the image plane (at the sensor array 50). The result is an image intensity shift in the image at the location of the defect. For example, in FIG. 10A the lens system of the camera 20 is represented by lens 88. Rays 90 and 91 emanate from point A, at the boundary between a clear and opaque stripe on the transition mask 32. These rays, which at the object 10 are designated as A', strike the lens 88 and are imaged at point A" on the sensor array 50. Similarly, rays 92 and 93 emanating from point B, at the boundary between a clear and opaque stripe on the transition mask, and designated at the object 20 as B', strike the lens 88 and are imaged at point B" on the sensor array 50. Rays 94 and 95 emanating from point C within a clear stripe, and designated by points C' on the object 20 focus to point C" on the sensor array 50.

Figure 10B:
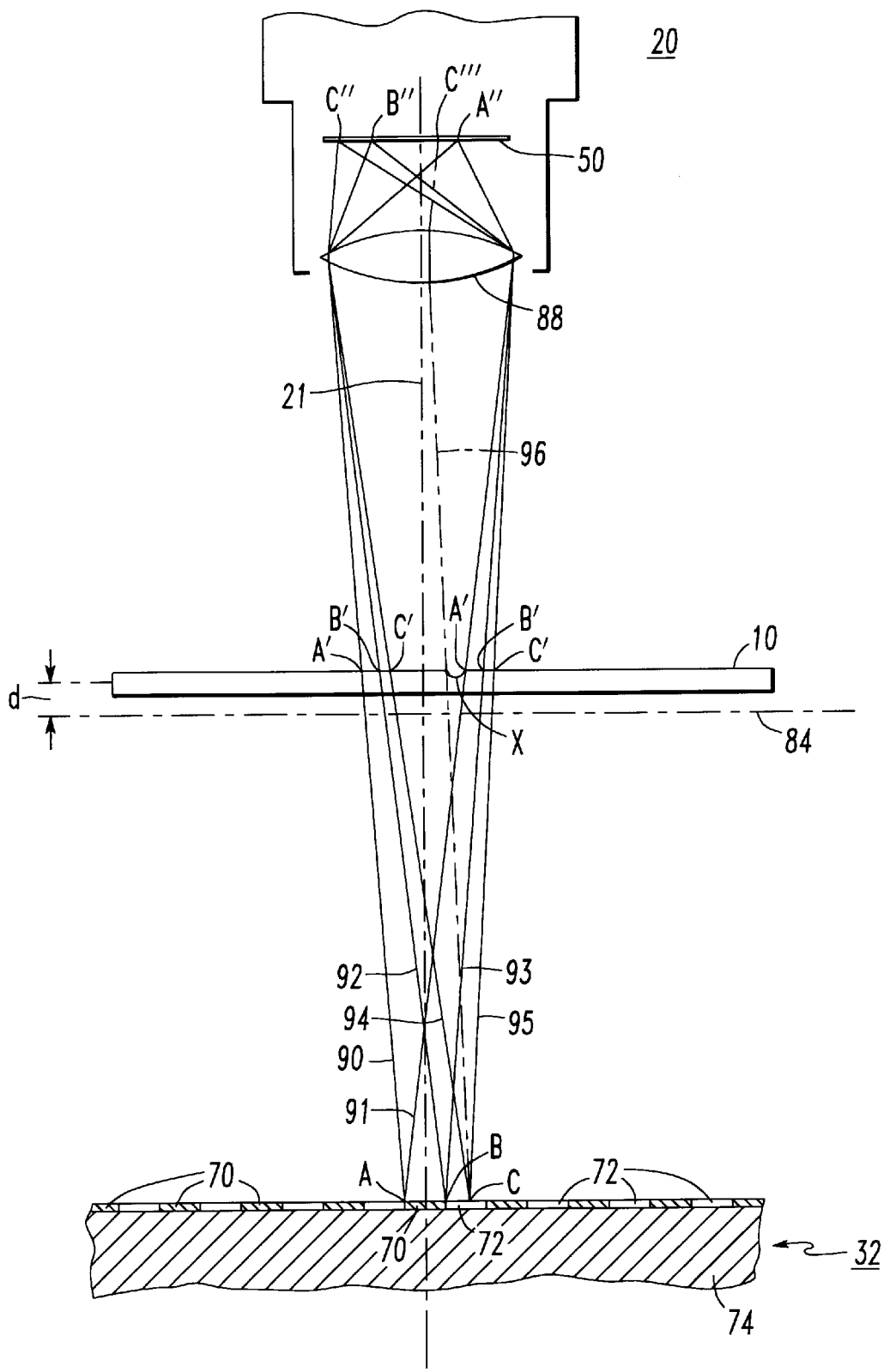

If a defect in the object 10 is present, such as at point X in FIG. 10B, it will cause a ray from point C which would normally be imaged at point C" to be redirected, as indicated by the dot-dashed ray 96, to a point C'" on the sensor array 50 causing a disruptive influence on the otherwise uniform image. The redirection of light is optimized by the alternating clear and dark stripe pattern because all defects are in close proximity to an opaque/clear boundary. In this regard, the stripe spacing is selected to be small to maximize this effect. By way of example, for examination of an object such as sheet glass, with a camera 20 having a 60 mm focal length lens with a field of view of 15 mm by 15 mm, a transition mask 32, located 70 mm behind the object, may have a dimension of 40 mm by 40 mm with a stripe spacing of less than 1 mm, for example 0.5 to 0.8 mm. The distance d may typically be around 4 mm.

Figure 10C:
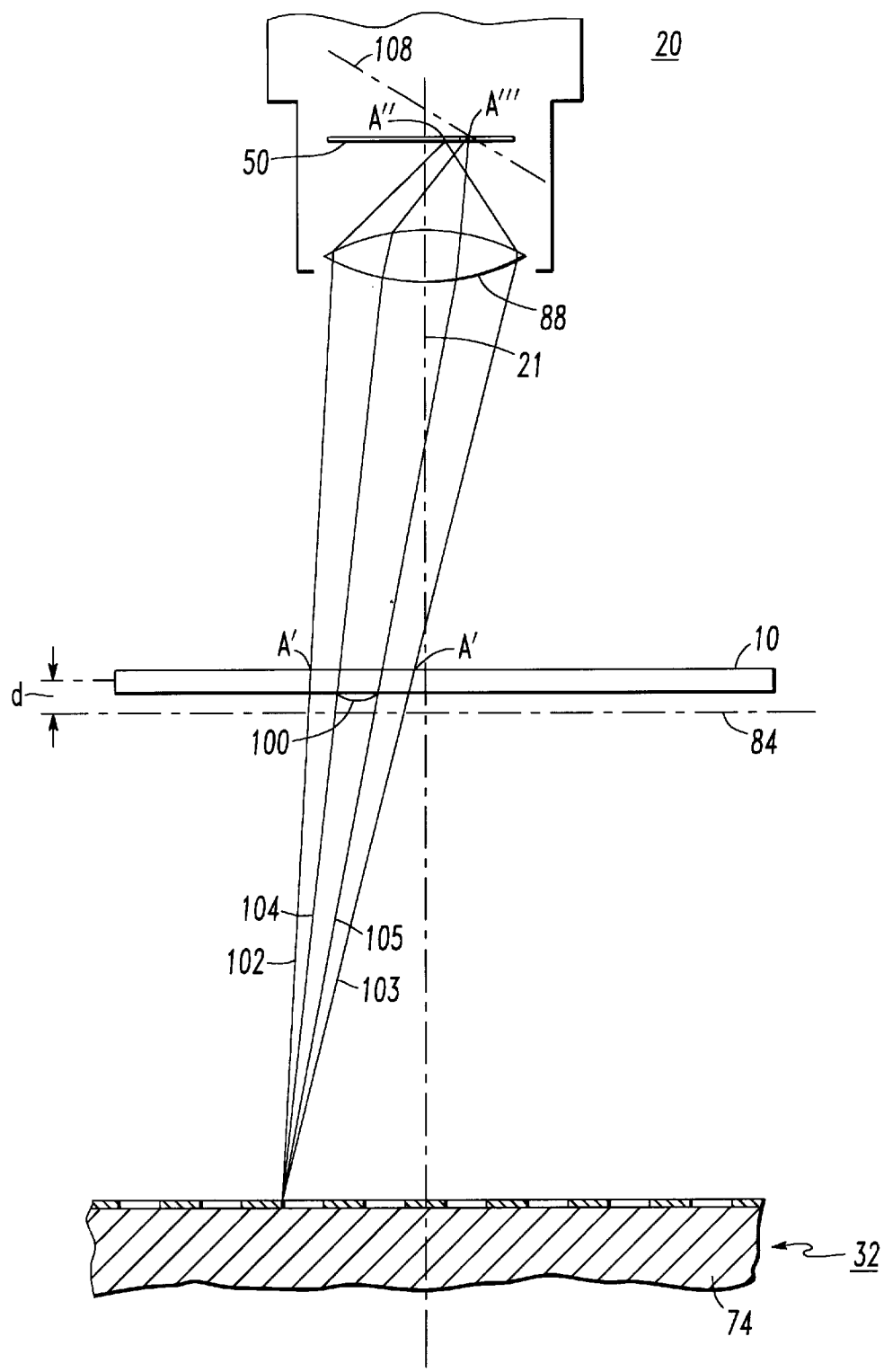

FIG. 10C illustrates another mechanism which causes an image shift. The object 10 to be inspected includes a defect 100 in the form of a protrusion essentially equivalent to a small lens having its own optical axis different from optical axis 21 of the camera 20.

Rays 102 and 103 emanate from point A on the transition mask 32, proceed through object 10, and are imaged at point A" on the sensor array 50. The defect 100 forming a small lens causes rays 104 and 105 emanating from the same point A on the transition mask 32 to proceed to point A'" on an image plane 108 of lens 100 and which image plane is skewed with respect to the image plane defined by the sensor array 50, resulting in detail shifts.

Figure 11:
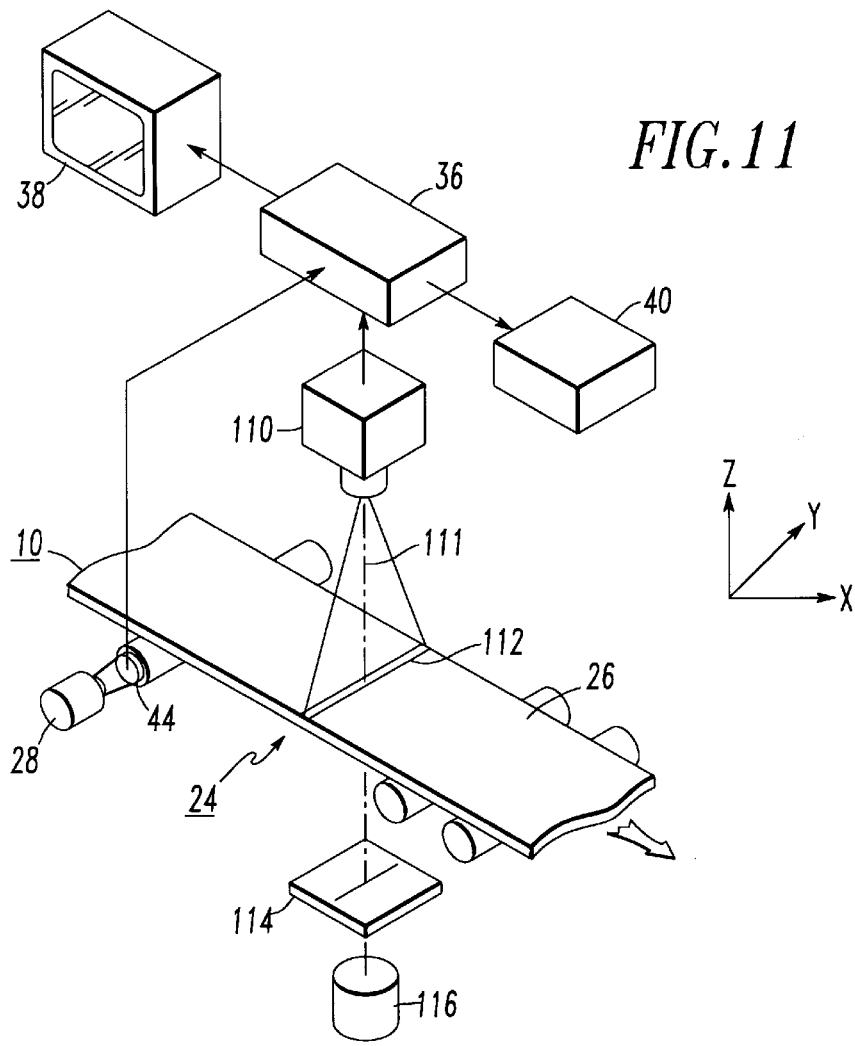
FIG. 11 illustrates another embodiment of the present invention.

FIG. 11 illustrates another embodiment of the invention which is more sensitive to defects and is somewhat easier to implement, set up and maintain. It is also less sensitive to variations in camera distance and mask distance from the object being inspected.

As can be seen, many of the components of FIG. 11 are similar to those of FIG. 4, however the camera 110 in the embodiment of FIG. 11 is a line scan camera having an optical axis 111. This camera obtains an image of the object being tested, one line at a time and thus the viewing area 112 for camera 110, at inspection location 24 is a single line. In addition, the mask 114, illuminated by light source 116, is comprised of a single stripe, as will be described. The light source 116 may be of the type which provides a conventional light or may be of the type which provides a monochromatic light.

For the embodiment of FIG. 11, by way of example, for examination of an object such as sheet glass, with a camera 110 having a 25 mm focal length lens examining a viewing area of 256 mm by 0.25 mm, a mask 114, located 50 mm behind the object, may have a stripe width of around 1.75 mm and a length equal to or greater than the 256 mm width being examined.

Figure 12:
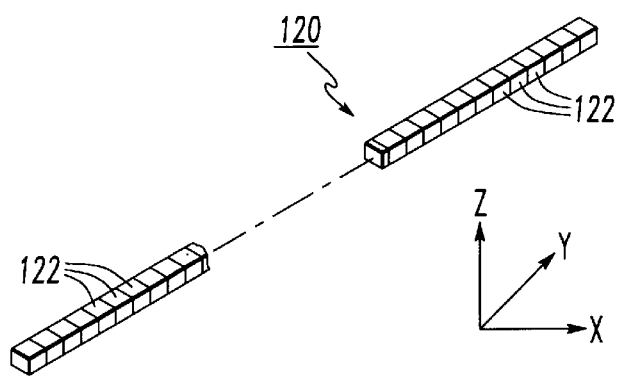
FIG. 12 illustrates a sensor array which is incorporated in the camera shown in FIG. 11.

FIG. 12 illustrates the sensor array 120 of camera 110. The sensor array 120 is a straight line array of individual sensor elements 122, typically ranging, in a commercially available camera, from 256 to 4096 CCD sensor elements, depending upon the resolution desired.

Figure 13A:
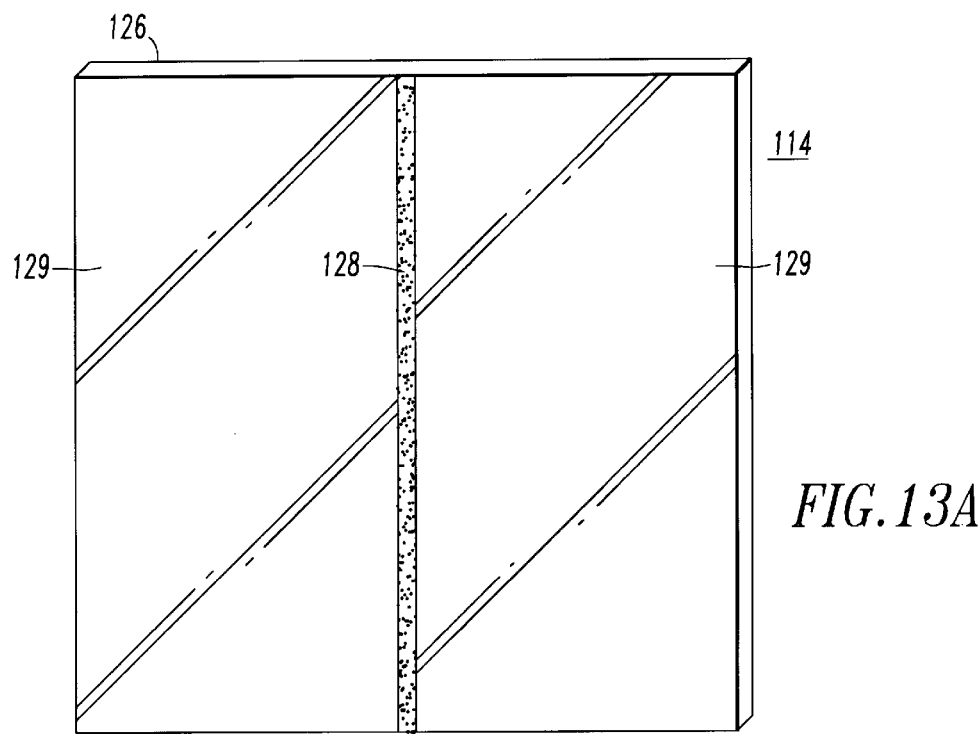
FIGS. 13A and 13B illustrate masks which may be utilized with the embodiment of FIG. 11.
Figure 13B:
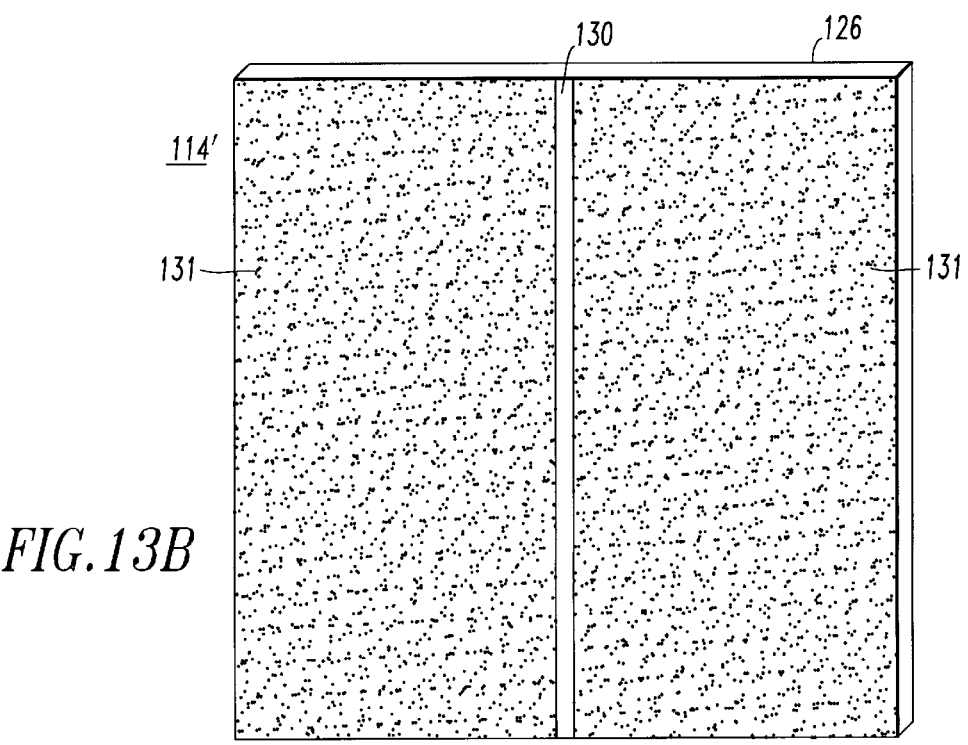

Light masks for this embodiment of the invention are illustrated in FIGS. 13A and 13B. In FIG. 13A, the mask 114 is on a diffuser plate 126 and is comprised of an opaque stripe 128, which blocks transmission of light, with the opaque stripe 128 being straddled by clear regions 129 which allow transmission of light. Conversely, mask 114' in FIG. 13B is comprised of a clear stripe 130 which allows transmission of light, straddled by light blocking opaque regions 131.

The stripe in the two different mask patterns will be the region observed by the line scan camera 110 when no object is present for inspection. For a mask 114 with an opaque stripe 128 the image of the object being inspected will have a black background in which any defects will show up as white. For a mask 114' with a clear stripe 130 the image of the object being inspected will have a white background in which any defects will show up as black. This may be observed with reference to FIGS. 14A, 14B and 15A,15B.

For the opaque stripe mask 114, defects are enhanced based upon an optimized dark field technique for which a dark field boundary between opaque and clear is always in close proximity to the defect in question. Similarly, For the clear stripe mask 114', defects are enhanced based upon an optimized bright field technique for which a bright field boundary between clear and opaque is always in close proximity to the defect in question. Both of these require light to be redirected only a slight amount by a defect in order for it to be detected.

Figure 14A:
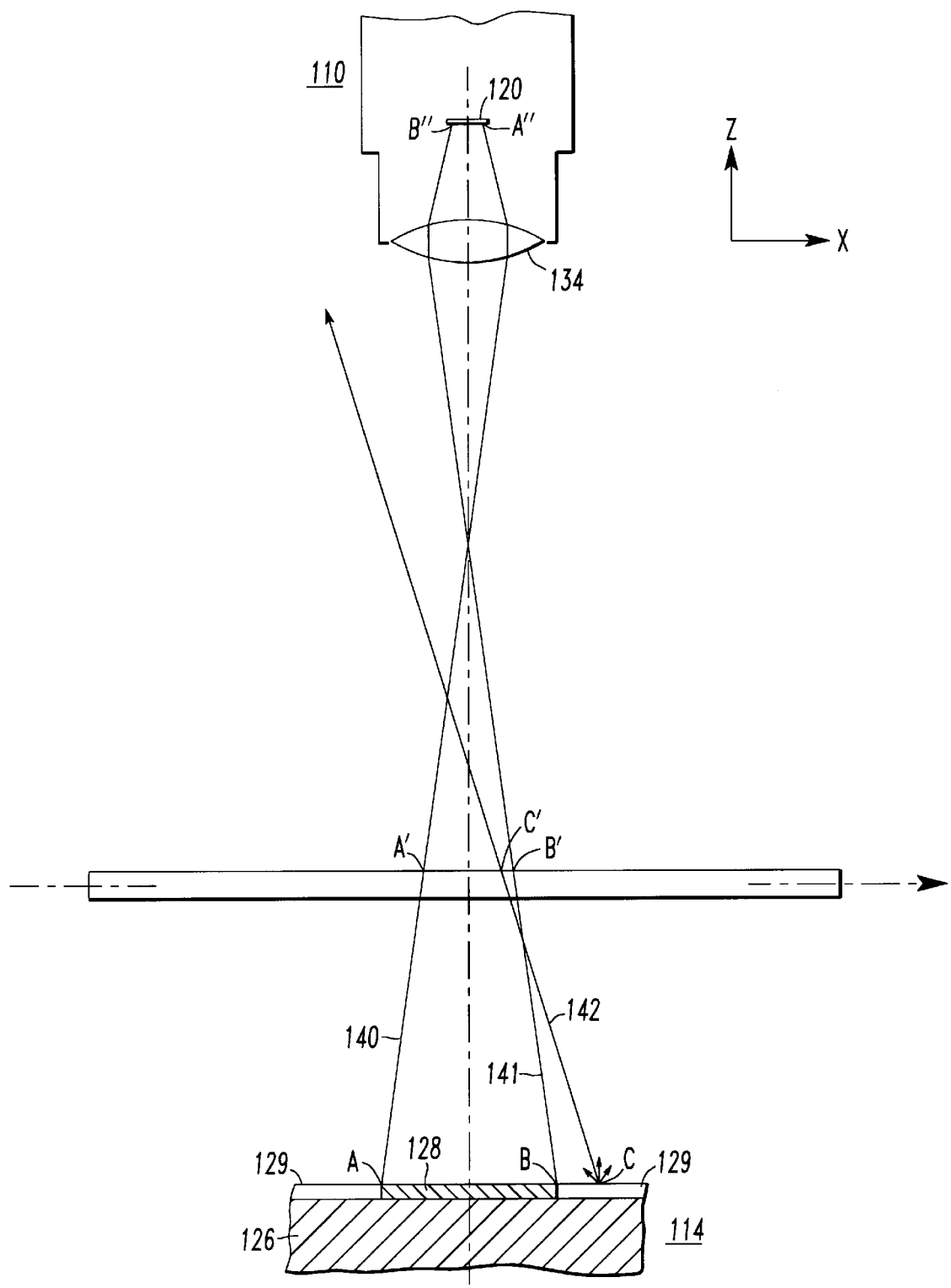
FIGS. 14A and 14B are ray diagrams illustrating the operation of the apparatus with a mask such as illustrated in FIG. 13A.

More particularly, FIG. 14A illustrates the use of an opaque stripe mask 114. The camera 110, having a lens system represented by lens 134, is focused at the object plane 136. For the examination procedure using the masks of FIGS. 13A and 13B the object 10 is positioned at the object plane 136, as opposed to above it. Ray 140 emanating from point A at the boundary of the opaque stripe 128 and clear region 129, strikes the moving object 10 at point A' and is imaged at the sensor line array 120, more particularly at one element thereof, at point A".

Similarly, ray 141 from point B passes through object 10 at point B' and is imaged at point B" at the sensor array 120. In the absence of a defect, a ray such as ray 142, from point C does not enter the camera, or if it does, it is at an angle which does not result in its being imaged at any sensor element.

Figure 14B:
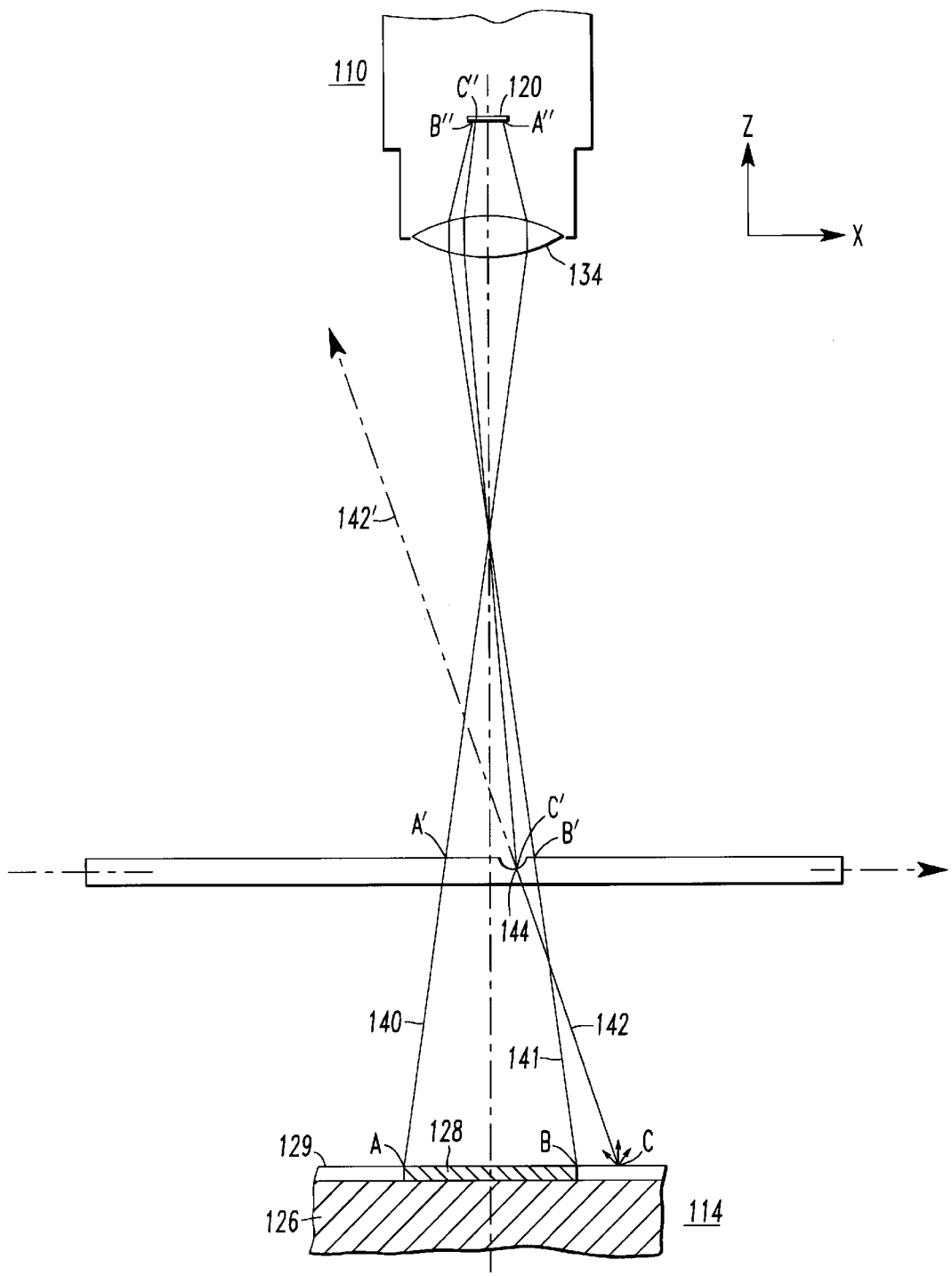

FIG. 14B illustrates the object 10 with a defect 144. Rays 140 and 141 from points A and B are imaged as before, however the ray 142 from point C rather than continuing as before (indicated by the dot dashed line 142') is now redirected by the defect 144 so as to be imaged at point C" on the sensor element, causing its output to vary from a signal which previously represented a completely dark area, to a signal which now represents a lighter area, due to the contribution of light from point C.

Figure 15A:
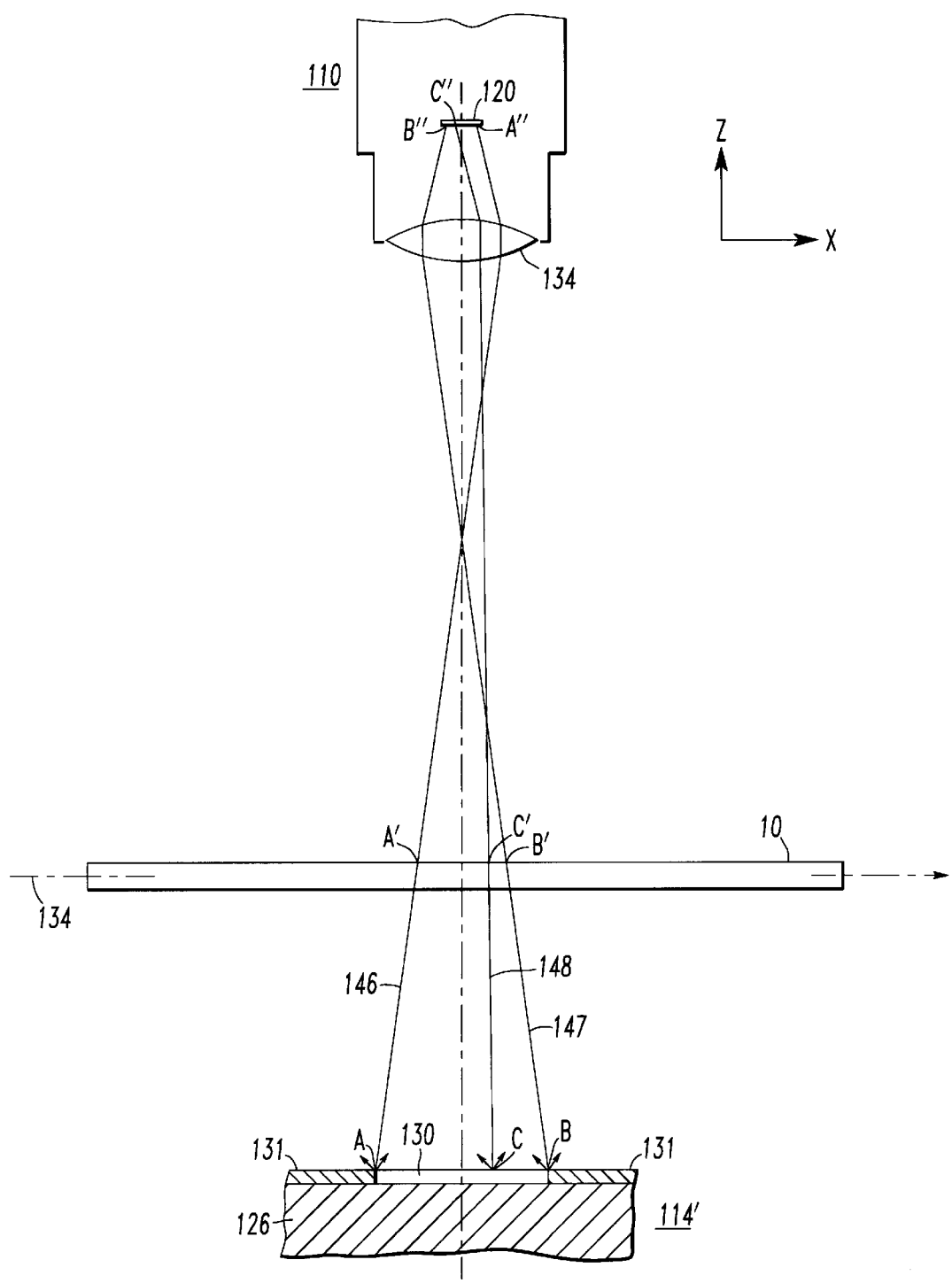
FIGS. 15A and 15B are ray diagrams illustrating the operation of the apparatus with a mask such as illustrated in FIG. 13B.
Figure 15B:
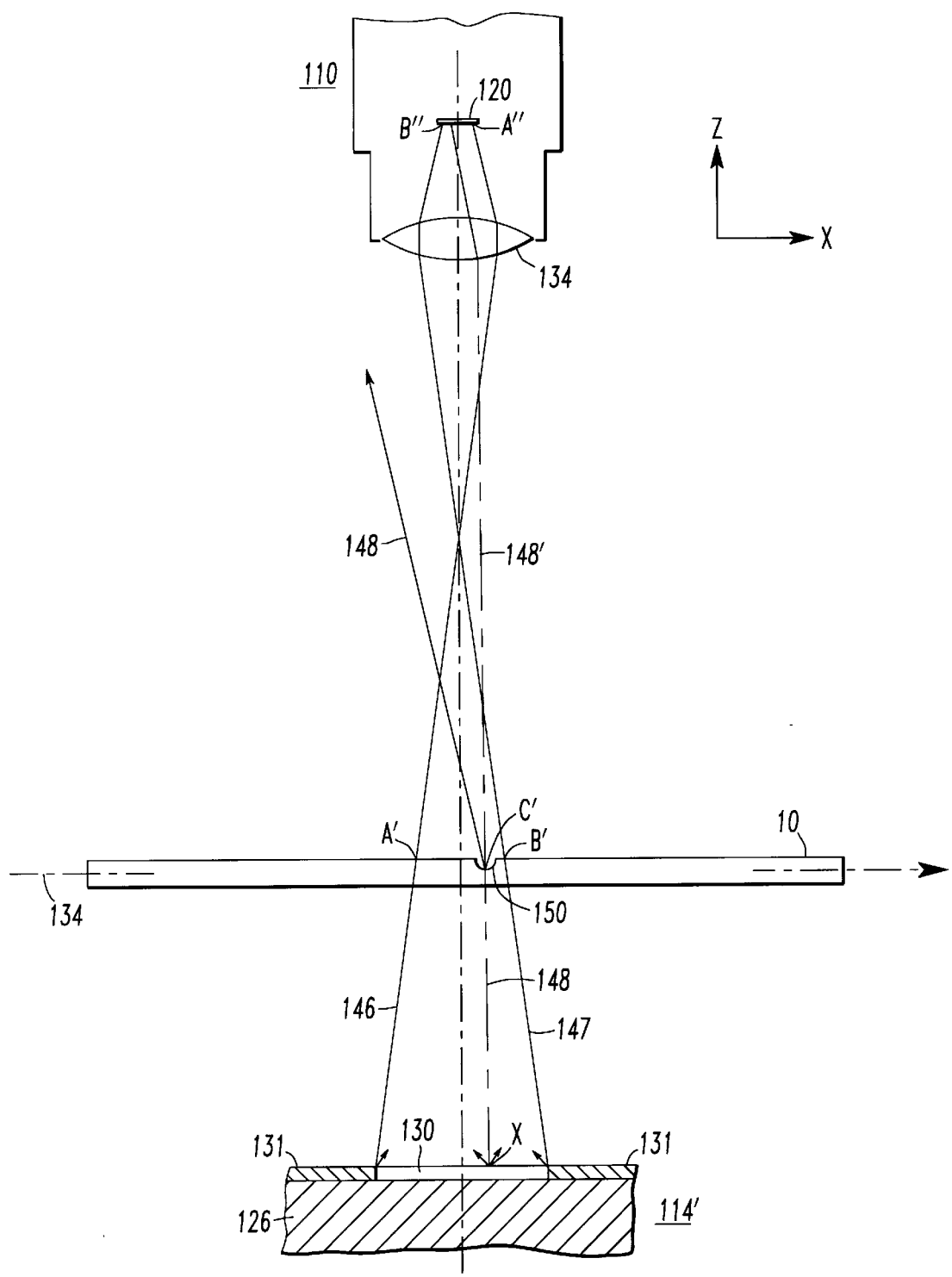

FIGS. 15A and 15B illustrate the concept utilizing a clear stripe mask 114'. In the absence of a defect, and as shown in FIG. 15A, boundary rays 146 and 147 from respective points A and B of the mask 114' pass through the object 10 at points A' and B'. These rays are directed to sensor array by the lens 134, where they are imaged at respective points A" and B". Any ray emanating from the clear stripe 130, such as ray 148 from point C will also be imaged at the sensor, as represented by point C", and thus the sensor element will provide an output signal indicative of a bright area.

FIG. 15B illustrates the object 10 with a defect 150. Rays 146 and 147 from points A and B are imaged as before, however the ray 148 from point C rather than continuing as before (indicated by the dot dashed line 148') is now redirected by the defect 150 so as to completely miss the sensor element, causing its output to vary from a signal which previously represented a completely bright area, to a signal which now represents a darker area, due to absence of the contribution of light from point C.

Figure 16A:
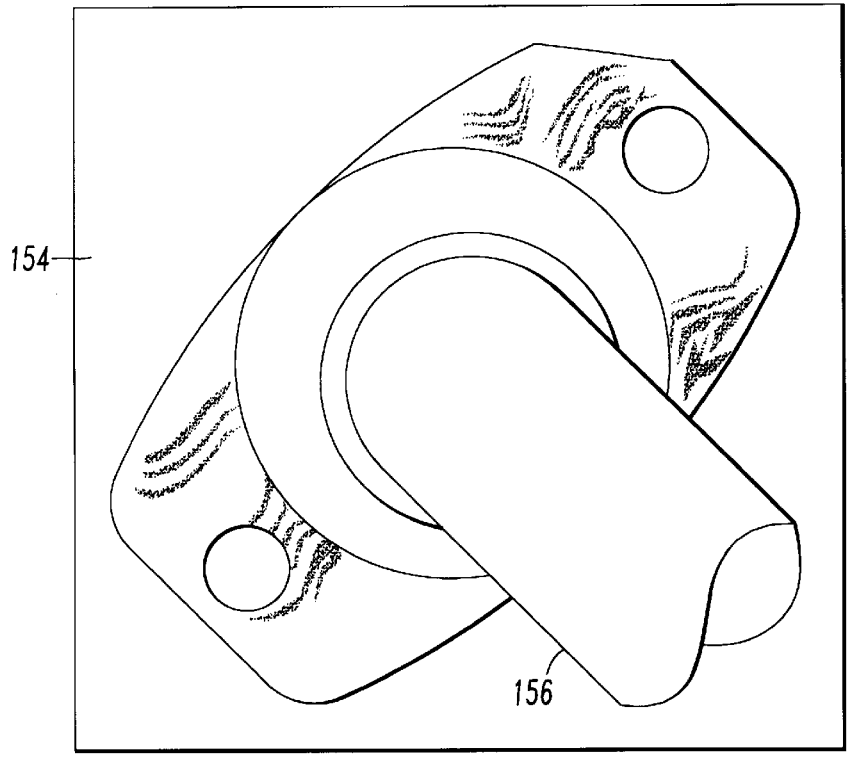
FIGS. 16A and 16B are displays of certain objects resulting from the use of a transition mask.
Figure 16B:
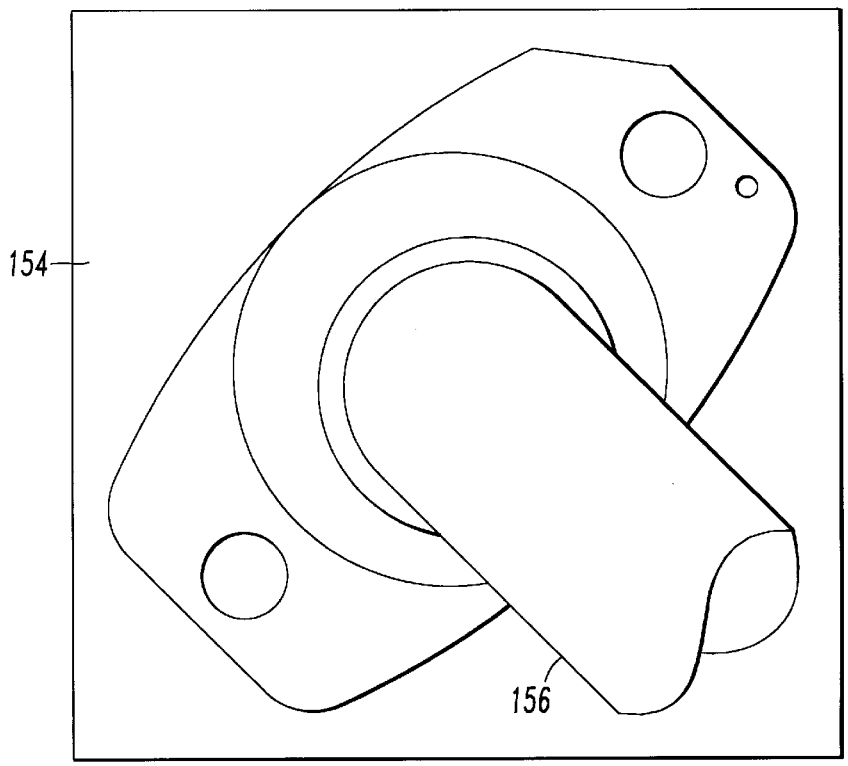

FIGS. 16A and 16B illustrate images obtained utilizing the transition mask of FIG. 7 with the planar haptic zone of an IOL (FIG. 3) being inspected. These displays show the essentially uniform background 154 upon which the camera is focused and reference numeral 156 is a vacuum pick up device for holding the IOL in the inspection location, as described in the aforementioned application. FIG. 16A illustrates typical flow mark defects and FIG. 16B illustrates a typical pit defect.

Although the present invention has been described with a certain degree of particularity, it is to be understood that various substitutions and modifications may be made without departing from the spirit and scope of the invention as defined in the appended claims.

What is claimed is:

1. Apparatus for determining defects in an optically transmissive planar object, comprising:
   (A) a camera having a sensor array for obtaining images of said object, said camera having an optical axis;
   (B) a light source positioned to direct light at said camera along said optical axis;
   (C) an object inspection location for receiving said object and disposed between said camera and said light source, said planar object being located at an object plane with said camera being focused at a position that is within the distance of several millimeters from said object plane;
   (D) a mask positioned in the light path between said light source and said inspection location;
   (E) said mask having a stripe design selected from the group consisting of a) a narrow clear stripe, for allowing transmission of said light, and straddled by opaque regions which block transmission of said light, b) a narrow opaque stripe straddled by clear regions and c) alternating narrow clear and opaque stripes of a spacing that will cyclically generate a uniform background through interference phenomenon in the region between said mask and said camera;
   (F) said camera being operable to obtain an image of said object with a selected one of said masks in position; and
   (G) means for processing said images to obtain indications of said defects.

2. Apparatus according to claim 1 wherein:
   (A) said light source provides monochromatic light.

3. Apparatus according to claim 2 wherein:
   (A) said mask is comprised of alternating narrow clear and opaque stripes; and wherein
   (B) said camera includes a planar sensor array to obtain an XY image;
   (C) said camera is focused at an object plane wherein the pattern of said mask appears as essentially uniform; and
   (D) said object is at a position displaced from said object plane.

4. Apparatus according to claim 3 wherein:
   (A) said object is above said object plane.

5. Apparatus according to claim 4 wherein:
   (A) said stripes are parallel.

6. Apparatus according to claim 1 which includes:
   (A) means for moving said object into said inspection location.

7. Apparatus according to claim 1 wherein:
   (A) said mask is comprised of a selected one of said clear stripe or opaque stripe designs;
   (B) said camera includes a sensor having a line array of sensor elements to obtain a line image; and which includes
   (C) means for continuously moving said object through said inspection location to build up an image of said object.

8. Apparatus according to claim 7 which includes:
   (A) encoder means coupled to said signal processor to provide said signal processor with positional information relative to said object, as said object moves through said inspection station.

9. Apparatus according to claim 7 wherein:
   (A) said line array is a straight line.

* * * * *